United States Patent
Roots

(10) Patent No.: US 9,220,453 B2
(45) Date of Patent: Dec. 29, 2015

(54) APPARATUS FOR MOUNTING A WIRELESS SENSOR ON A HUMAN FOR DIAGNOSING AND TREATING COGNITIVE DISORDERS

(71) Applicant: Kurt Edward Roots, Minneapolis, MN (US)

(72) Inventor: Kurt Edward Roots, Minneapolis, MN (US)

(73) Assignee: COGCUBED CORPORATION, Minneapolis, MN (US)

(*) Notice: Subject to any disclaimer, the term of this patent is extended or adjusted under 35 U.S.C. 154(b) by 135 days.

(21) Appl. No.: 13/967,136

(22) Filed: Aug. 14, 2013

(65) Prior Publication Data

US 2013/0331737 A1 Dec. 12, 2013

Related U.S. Application Data

(63) Continuation-in-part of application No. 13/657,332, filed on Oct. 22, 2012, now Pat. No. 9,014,614.

(60) Provisional application No. 61/719,280, filed on Oct. 26, 2012, provisional application No. 61/683,532, filed on Aug. 15, 2012, provisional application No. 61/549,698, filed on Oct. 20, 2011, provisional application No. 61/551,384, filed on Oct. 25, 2011.

(51) Int. Cl.
| | |
|---|---|
| G09B 7/00 | (2006.01) |
| A61B 5/16 | (2006.01) |
| A61B 5/11 | (2006.01) |
| A61B 5/00 | (2006.01) |
| G09B 5/06 | (2006.01) |

(52) U.S. Cl.
CPC .............. *A61B 5/168* (2013.01); *A61B 5/0004* (2013.01); *A61B 5/11* (2013.01); *A61B 5/6824* (2013.01); *A61B 5/6829* (2013.01); *G09B 5/06* (2013.01)

(58) Field of Classification Search
CPC .................... A61B 2562/0219; A61B 5/6829; A61B 15/681; A61B 15/6835; A63B 24/0062; A63B 2220/836; A63B 2220/803
USPC .......... 434/247, 362; 224/218, 219, 221, 222, 224/930
See application file for complete search history.

(56) References Cited

U.S. PATENT DOCUMENTS

| | | | | |
|---|---|---|---|---|
| 6,016,942 | A * | 1/2000 | Allen | 224/197 |
| 6,334,778 | B1 | 1/2002 | Brown | |
| 8,827,915 | B1 * | 9/2014 | Bady et al. | 600/500 |
| 2008/0091474 | A1 | 4/2008 | Ober et al. | |
| 2008/0280276 | A1 | 11/2008 | Raber et al. | |
| 2009/0273560 | A1 * | 11/2009 | Kalanithi et al. | 345/156 |
| 2012/0258436 | A1 | 10/2012 | Lee | |

FOREIGN PATENT DOCUMENTS

WO 2012064999 A1 5/2012

* cited by examiner

*Primary Examiner* — Sam Yao
*Assistant Examiner* — Jerry-Daryl Fletcher
(74) *Attorney, Agent, or Firm* — Edward P. Heller, III

(57) ABSTRACT

A cognitive disorder diagnostic and treatment system having a plurality of wireless sensors strapped to the arms and legs of a human being for improved diagnostic capability. The wireless sensors are in the form of cubes which are mounted on apparatus comprising a pair clips, and a Velcro strap. The strap is connected to the mounting apparatus through angled apertures whereby the top surface of the wireless sensor is canted toward the user for better visibility of graphics which are displayed on the top surface of the sensor.

6 Claims, 3 Drawing Sheets

APPARATUS FOR MOUNTING A WIRELESS SENSOR ON A HUMAN FOR DIAGNOSING AND TREATING COGNITIVE DISORDERS

The present application claims the benefit of U.S. provisional application No. 61/683,532, filed 15 Aug. 2012; U.S. provisional application No. 61/719,280, filed 26 Oct. 2012; and is a continuation-in-part of U.S. patent application Ser. No. 13/657,332, filed 22 Oct. 2012, which claims the benefit of provisional application Nos. 61/549,698, filed 20 Oct. 2011, and 61/551,384, filed 25 Oct. 2011; the contents of which are hereby incorporated by reference in their entirety.

BACKGROUND OF THE INVENTION

1. Field of the Invention

The invention relates to the field of apparatus and methods for determining and treating cognitive disorders including attention deficits and/or cormorbidities, treating attention-deficit hyperactivity disorder, and/or conditions with attentional impairment such as autism spectrum disorder (ASD), anxiety, depression and epilepsy.

2. Background of the Art

The co-pending and priority applications disclose apparatus and methods for determining and treating cognitive orders using an interactive system of graphics and sounds employed on a plurality of wireless sensors that each contain accelerometers, Bluetooth/near field transducers, LCD screens, buttons microprocessor and wireless input-output means for communicating to a base station. The sensors are commercially available as Sifteo cubes, hereinafter "cubes", whereby a patient is prompted to play a game that has predetermined activity. The player must manipulate the cubes in response to stimuli and direction. His ability to do so is affected by and indicative of cognitive disorders. The cubes communicate to a base station where the data is recorded and analyzed statistically to determine whether the patient may be suffering from a cognitive disorder. Similarly, the cubes may be programmed with games and or other activity that causes the patient to engage in activity that may treat a diagnosed cognitive disorder.

SUMMARY OF THE INVENTION

The present invention seeks to extend the range of activities that can be monitored in a patient by providing apparatus for mounting the wireless, interactive, and graphical sensors on the patient at strategic locations including for example their wrists and ankles that their movements in response to stimuli may be recorded and analyzed, and which may also be utilized in manipulating other graphics such as conventional and 3-D displays associated with the cubes to create a virtual environment. For example, the patient may be asked to play a 3-D game and the locations of the arms and legs in the virtual universe may be determined using the mounted cubes whereby activity a location of the patient in the 3-D world may be updated and new stimuli may be introduced.

DETAILED DESCRIPTION

Figure 1:
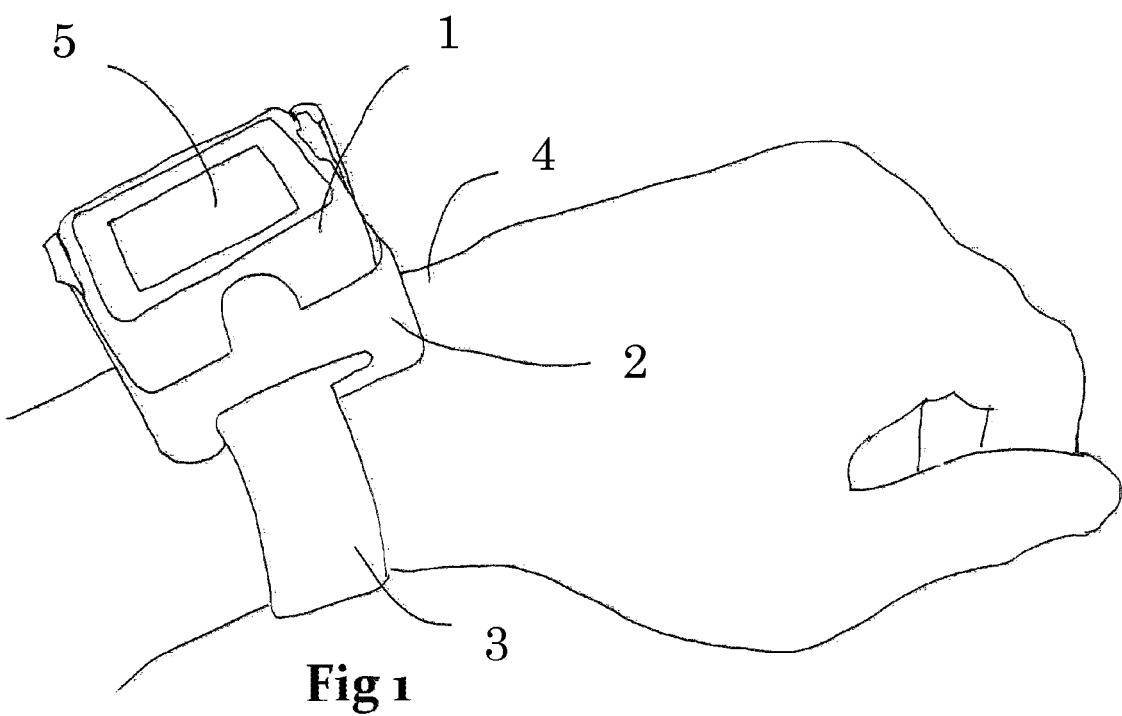
FIG. 1 illustrates a mounted, wireless sensor strapped to the wrist of a human being.

FIG. 1 illustrates a wireless sensor 1, preferably in the form of a Sifteo cube, mounted in a mounting fixture 2, strapped via a strap 3 the wrist 4 of a human being. It is intended that the same mounting fixture 2 be used to mount additional wireless sensors to the other wrist, and or to the ankles of the person.

Figure 2:
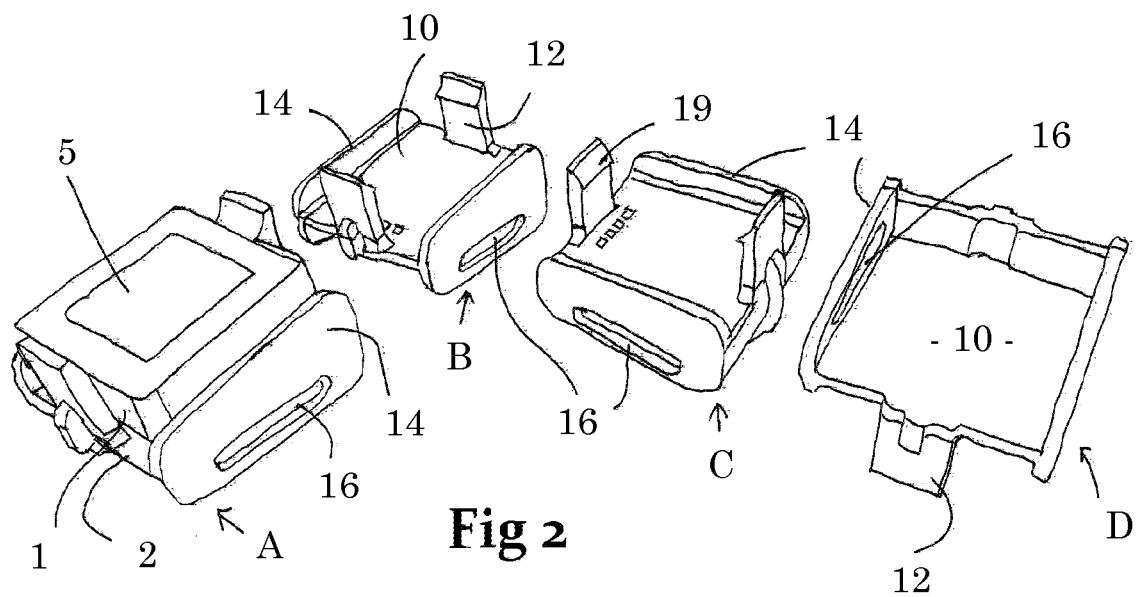
FIGS. 2A-2D comprise perspectives of the fixture, a first showing a wireless sensor mounted in a mounting fixture, a first orientation of the mounting fixture, a second orientation the mounting fixture, and a mounting fixture inverted.

FIG. 2, views A, B, C and D, illustrate the mounting apparatus 2 in various perspectives. In view A, a wireless sensor 1 is shown mounted on a mounting apparatus to. In a mounted arrangement, the wireless sensor is held against a surface 10 by clips 12, which are comprised of opposed, resilient beams having a an edge/clip 19 (see FIGS. 2/3). The clips are mounted on opposite sides of the mounting surface 10. The mounting sensor is also constrained by constraints 14 which are opposed walls mounted on the mounting surface 10 edges caddy corner to the mounting clips 12. These opposed walls 14 extend vertically up from the mounting surface 10 a short distance to act as constraints for the wireless sensor, and down from the mounting surface a short distance to support a strap aperture 16. The strap 3, shown in FIG. 1, may be inserted through the apertures 16 in the opposed walls 14. The strap 3 is preferably composed of Velcro.

Figure 3:
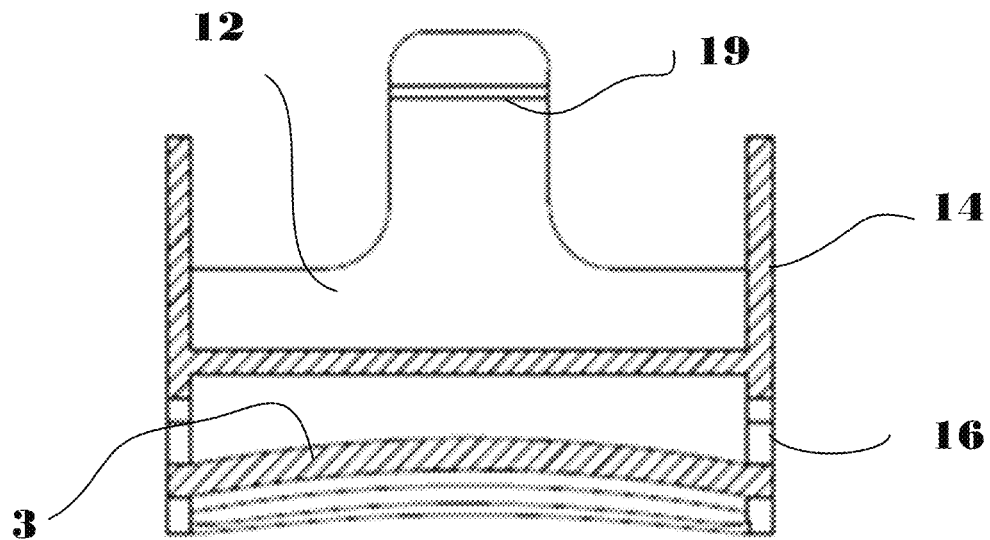
FIG. 3 is a cross-section of a mounting fixture from a first direction.

FIG. 3 shows a cross-section of a mounting fixture 2. The figure illustrates that the opposed walls extend a short distance above the mounting surface 10 to act as constraints, and a short distance below the mounting surface 10 to provide strap apertures 16. Strap 3 is show spanning the gap between apertures 16. It is shown with the arcuate shape that it would take when mounted on the wrist of a human as illustrated in FIG. 1. The figure also shows the vertically extending clip 12 having a clip edge 19.

Figure 4:
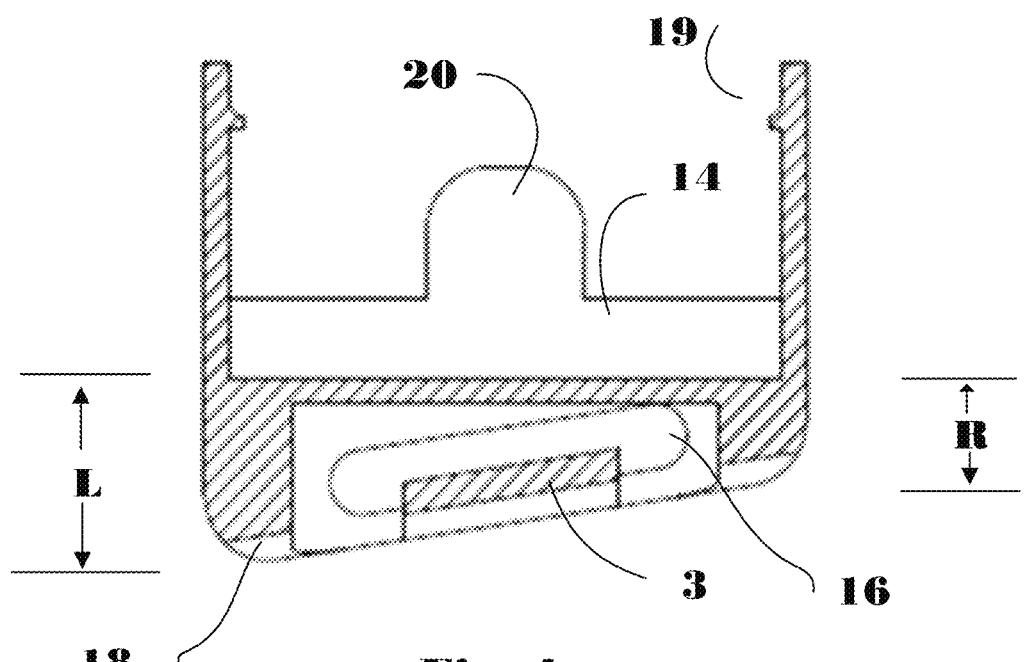
FIG. 4 is a cross-section of the mounting fixture from a second direction.

FIG. 4 shows a cross-section of the mounting fixture 2 from a second cross-section. This shows the clips 12 transversely having near their tops clipped edges 19. The figure also shows the opposing wall 14 extends above the mounting surface 10. It preferably has a centrally located 20 extending further for writing further constraints on a wireless sensor. The opposing wall is also shown that it sides extend in two different lengths L and R below mounting surface 10 so that it's bottom edge forms an oblique angle with the mounting surface 10. The opposing wall bears an aperture 16 through which strap 3 may extend. The aperture is preferably aligned with the bottom edge 18 of the opposing wall 14 says that it too has an oblique angle with the mounting surface 10. The angle is chosen such as to cant the top surface 5 of the wireless sensor 1 toward the user when the wireless sensor 1 is mounted on the wrist 4 of that user. This top surface employs an active graphical display that displays graphics that may be transmitted from the base station as described in the parent applications. The canting of this top surface 5 improves the visibility of these graphics to the user.

The invention contemplates strapping at least two, and preferably four, wireless sensors to a human to monitor the motion of their arms and preferably their legs in response to predetermined programmed activity transmitted from the base station (not shown). This permits improved diagnosis of cognitive disorders, and improved methods of treating such as described in the parent applications.

The invention claimed is:

1. In a cognitive disorder diagnosis and treatment system having a base station and a plurality of wireless sensors each comprising accelerometers that may communicate with the base station wirelessly and may display graphics transmitted from the base station, an improvement comprising:
- a plurality of fixtures for mounting a wireless sensor and for strapping to the limb of a human being;
- wherein each of said plurality of fixtures comprises:
- a mounting surface having first and second opposed edges;
- a pair of walls mounted one each to the mounting surface at the first opposed edges;
- a pair of resilient clips mounted one each to the mounting surface at the second opposed edges;
- wherein each of the pair of walls has an aperture through which a strap may extend; and further wherein
- each of the walls has two sides and a bottom edge, wherein each side has a different length measured from the mounting surface whereby its bottom edge forms an oblique angle relative to mounting surface.

2. The system of claim 1, wherein individual of the plurality of fixtures, each mounting a wireless sensor, are strapped to at least the wrists and ankles of a human being.

3. The system of claim 1, wherein a strap comprises Velcro.

4. In a cognitive disorder diagnosis and treatment system having a base station and a plurality wireless sensors each comprising accelerometers that may communicate with the base station wirelessly and may display graphics transmitted from the base station, an improvement comprising:
- a plurality of fixtures for mounting a wireless sensor and for strapping to the limb of human being;
- wherein each of said plurality of fixtures comprises.
- a mounting surface having first and second opposed edges;
- a pair of walls mounted one each to the mounting surface at the first opposed edges;
- a pair of resilient clips mounted one each to the mounting surface at the second opposed edges;
- wherein each of the pair of walls has an aperture through which a strap may extend; wherein the aperture in a wall is aligned with the bottom edge of the wall thereby forming an oblique angle relative to the mounting surface.

5. The system of claim 4, wherein a strap comprises Velcro.

6. The system of claim 4, wherein individual of the plurality of fixtures, each mounting a wireless sensor, are strapped to at least the wrists and ankles of a human being.

* * * * *